(12) United States Patent
Wiederin et al.

(10) Patent No.: US 10,500,583 B2
(45) Date of Patent: Dec. 10, 2019

(54) SYSTEMS AND METHODS FOR INLINE, DUAL-STAGE SAMPLE DILUTION

(71) Applicant: Elemental Scientific, Inc., Omaha, NE (US)

(72) Inventors: Daniel R. Wiederin, Omaha, NE (US); Austin Schultz, Omaha, NE (US)

(73) Assignee: Elemental Scientific, Inc, Omaha, NE (US)

( * ) Notice: Subject to any disclaimer, the term of this patent is extended or adjusted under 35 U.S.C. 154(b) by 0 days.

(21) Appl. No.: 16/119,228

(22) Filed: Aug. 31, 2018

(65) Prior Publication Data

US 2019/0070601 A1    Mar. 7, 2019

Related U.S. Application Data

(60) Provisional application No. 62/555,323, filed on Sep. 7, 2017.

(51) Int. Cl.
| | |
|---|---|
| *G01N 1/00* | (2006.01) |
| *B01L 3/00* | (2006.01) |
| *G01N 1/38* | (2006.01) |
| *G01N 21/73* | (2006.01) |
| *H01J 49/04* | (2006.01) |

(Continued)

(52) U.S. Cl.
CPC .............. *B01L 3/502* (2013.01); *B01L 3/523* (2013.01); *B01L 3/567* (2013.01); *G01N 1/38* (2013.01); *G01N 21/73* (2013.01); *G01N 35/1097* (2013.01); *H01J 49/0431* (2013.01); *B01L 2200/0605* (2013.01); *B01L 2300/024* (2013.01); *B01L 2300/049* (2013.01); *B01L 2300/0806* (2013.01); *B01L 2300/0861* (2013.01); *B01L 2300/0867* (2013.01); *B01L 2400/049* (2013.01); *B01L 2400/0487* (2013.01); *B01L 2400/06* (2013.01); *G01N 21/71* (2013.01); *G01N 2001/386* (2013.01);

(Continued)

(58) Field of Classification Search
CPC .......... B01L 3/502; B01L 3/523; B01L 3/567; G01N 1/38; G01N 21/73; G01N 35/1097; H01J 49/0431
USPC .......................................................... 356/36
See application file for complete search history.

(56) References Cited

U.S. PATENT DOCUMENTS

| | | | | |
|---|---|---|---|---|
| 6,813,568 | B2 * | 11/2004 | Powell | ................ B01J 19/0046 422/521 |
| 8,414,774 | B2 * | 4/2013 | LaMarr | ................ G01N 30/24 210/141 |

(Continued)

*Primary Examiner* — Roy M Punnoose
(74) *Attorney, Agent, or Firm* — Kevin E. West; Advent, LLP (57) ABSTRACT

Sample preparation systems and methods are described having pump control, valve configurations, and control logic that facilitate automatic, inline preparation dilutions of a sample according to at least two dilution operating modes. A system embodiment includes, but is not limited to a first pump configured to drive a carrier fluid; a second pump configured to drive a diluent; and a plurality of selection valves fluidically coupled with the first pump and the second pump, the plurality of selection valves being configured to direct fluid flows from the first pump and the second pump according to at least two modes of operation to provide a single-stage sample dilution according to a first operating mode and to provide a dual-stage sample dilution according to a second operating mode.

20 Claims, 4 Drawing Sheets

(51) Int. Cl.
   *G01N 35/10* (2006.01)
   *H01J 49/10* (2006.01)
   *G01N 21/71* (2006.01)

(52) U.S. Cl.
   CPC .... *G01N 2035/1032* (2013.01); *H01J 49/105* (2013.01)

(56) References Cited

U.S. PATENT DOCUMENTS

| | | | | |
|---|---|---|---|---|
| 9,024,635 | B2* | 5/2015 | Dourdeville | G01N 24/08 324/309 |
| 9,177,772 | B1* | 11/2015 | Wiederin | H01J 49/105 |
| 10,192,726 | B1* | 1/2019 | Wiederin | H01J 49/0454 |
| 2010/0024527 | A1* | 2/2010 | LaMarr | G01N 30/24 73/61.56 |
| 2017/0209812 | A1* | 7/2017 | Dlugasch | B01D 15/1878 |
| 2017/0325623 | A1* | 11/2017 | Lyall, III | A47J 31/41 |

* cited by examiner

SYSTEMS AND METHODS FOR INLINE, DUAL-STAGE SAMPLE DILUTION

CROSS-REFERENCE TO RELATED APPLICATIONS

The present application claims the benefit of 35 U.S.C. § 119(e) of U.S. Provisional Application Ser. No. 62/555,323, filed Sep. 7, 2017, and titled "SYSTEMS AND METHODS FOR INLINE, DUAL-STAGE SAMPLE DILUTION." U.S. Provisional Application Ser. No. 62/555,323 is herein incorporated by reference in its entirety.

BACKGROUND

Inductively Coupled Plasma (ICP) spectrometry is an analysis technique commonly used for the determination of trace element concentrations and isotope ratios in liquid samples. ICP spectrometry employs electromagnetically generated partially ionized argon plasma which reaches a temperature of approximately 7,000K. When a sample is introduced to the plasma, the high temperature causes sample atoms to become ionized or emit light. Since each chemical element produces a characteristic mass or emission spectrum, measuring the spectra of the emitted mass or light allows the determination of the elemental composition of the original sample.

Sample introduction systems may be employed to introduce the liquid samples into the ICP spectrometry instrumentation (e.g., an Inductively Coupled Plasma Mass Spectrometer (ICP/ICP-MS), an Inductively Coupled Plasma Atomic Emission Spectrometer (ICP-AES), or the like) for analysis. For example, a sample introduction system may withdraw an aliquot of a liquid sample from a container and thereafter transport the aliquot to a nebulizer that converts the aliquot into a polydisperse aerosol suitable for ionization in plasma by the ICP spectrometry instrumentation. Prior or during transportation of the aliquot to the nebulizer, the sample aliquot may be mixed with hydride generation reagents and fed into a hydride gas/liquid separator that channels hydride and/or sample gas into the nebulizer. The aerosol generated by the nebulizer is then sorted in a spray chamber to remove the larger aerosol particles. Upon leaving the spray chamber, the aerosol is introduced into the plasma by a plasma torch assembly of the ICP-MS or ICP-AES instruments for analysis.

SUMMARY

Sample preparation systems and methods for dilution of fluid samples are described, where the samples are diluted inline in single or multi-stage dilution processes to achieve extreme accuracy in high dilution factors (e.g., dilution factors of 10,000 times and greater). A system embodiment includes, but is not limited to a first pump configured to drive a carrier fluid; a second pump configured to drive a diluent; and a plurality of selection valves fluidically coupled with the first pump and the second pump, the plurality of selection valves being configured to direct fluid flows from the first pump and the second pump according to at least two modes of operation to provide a single-stage sample dilution according to a first operating mode and to provide a dual-stage sample dilution according to a second operating mode.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The Detailed Description is described with reference to the accompanying figures. The use of the same reference numbers in different instances in the description and the figures may indicate similar or identical items.

DETAILED DESCRIPTION

Overview

Determination of trace elemental concentrations or amounts in a sample can provide an indication of purity of the sample, or an acceptability of the sample for use as a reagent, reactive component, or the like. For instance, in certain production or manufacturing processes (e.g., mining, metallurgy, semiconductor fabrication, pharmaceutical processing, etc.), the tolerances for impurities can be very strict, for example, on the order of fractions of parts per billion. In order to accurately measure trace elemental compositions for highly concentrated samples (e.g., metal ores, metallurgical compositions, etc.), the samples to be measured often require dilution for analysis by ICP spectrometry instrumentation (an Inductively Coupled Plasma Mass Spectrometer (ICP/ICP-MS), an Inductively Coupled Plasma Atomic Emission Spectrometer (ICP-AES), or the like)). For instance, if a sample is too concentrated, the sample could saturate the cones of the ICP spectrometry instrumentation, carry over undesirable background between samples, or ruin the instrumentation. However, obtaining accurate dilution factors can be difficult to achieve, particularly where manual techniques often involve relatively large volumes of liquids (e.g., 50 mL or more), delicate pipets or volumetric flasks, instrumentation requiring frequent certification, substantial time requirements, or the like. Moreover, for large dilution factors (e.g., 100× dilution and larger), the accuracy of a dilution can be limited by the resolution of a given pump (e.g., syringe pump, peristaltic pump, etc.), where such pumps may not have adequate resolution to provide consistent and accurate dilutions for multiple samples, standards, or the like.

Accordingly, the present disclosure is directed to systems and methods for inline, multi-stage dilution of a sample. The systems and methods can utilize multiple independent pumps fluidically connected to a valve system to dynamically alter a dilution factor for a given fluid (e.g., under computer control), where the dilution factor and number of dilution stages can vary between samples, standards, etc. The systems and methods accurately control carrier, diluent, and sample flows for dilution of fluids in the systems for analysis by ICP spectrometry instrumentation, as discussed in further detail below.

Example Implementations

Figure 1:
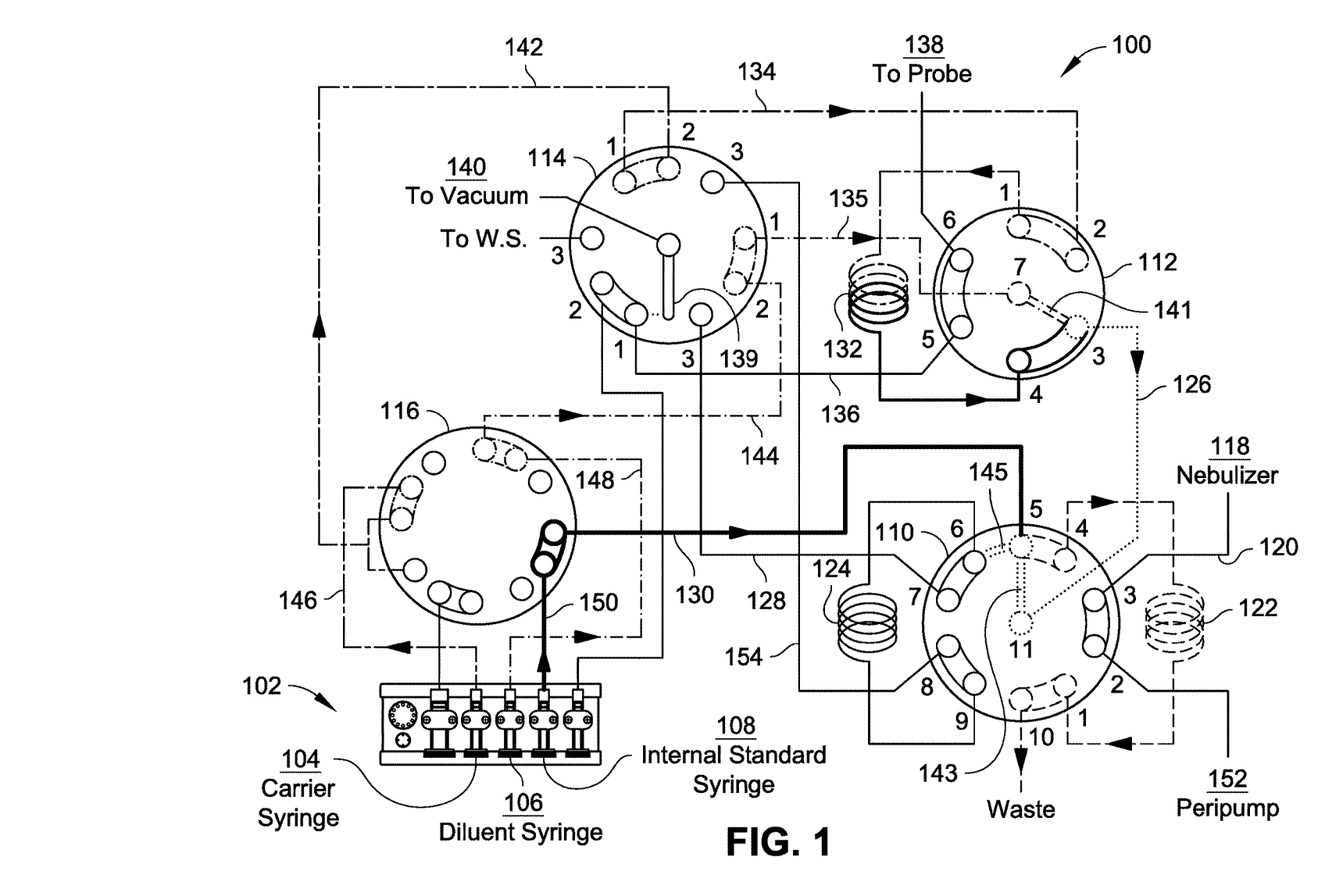
FIG. 1 is a schematic of a sample preparation system operating in a first sample dilution mode, in accordance with an embodiment of this disclosure.
Figure 2:
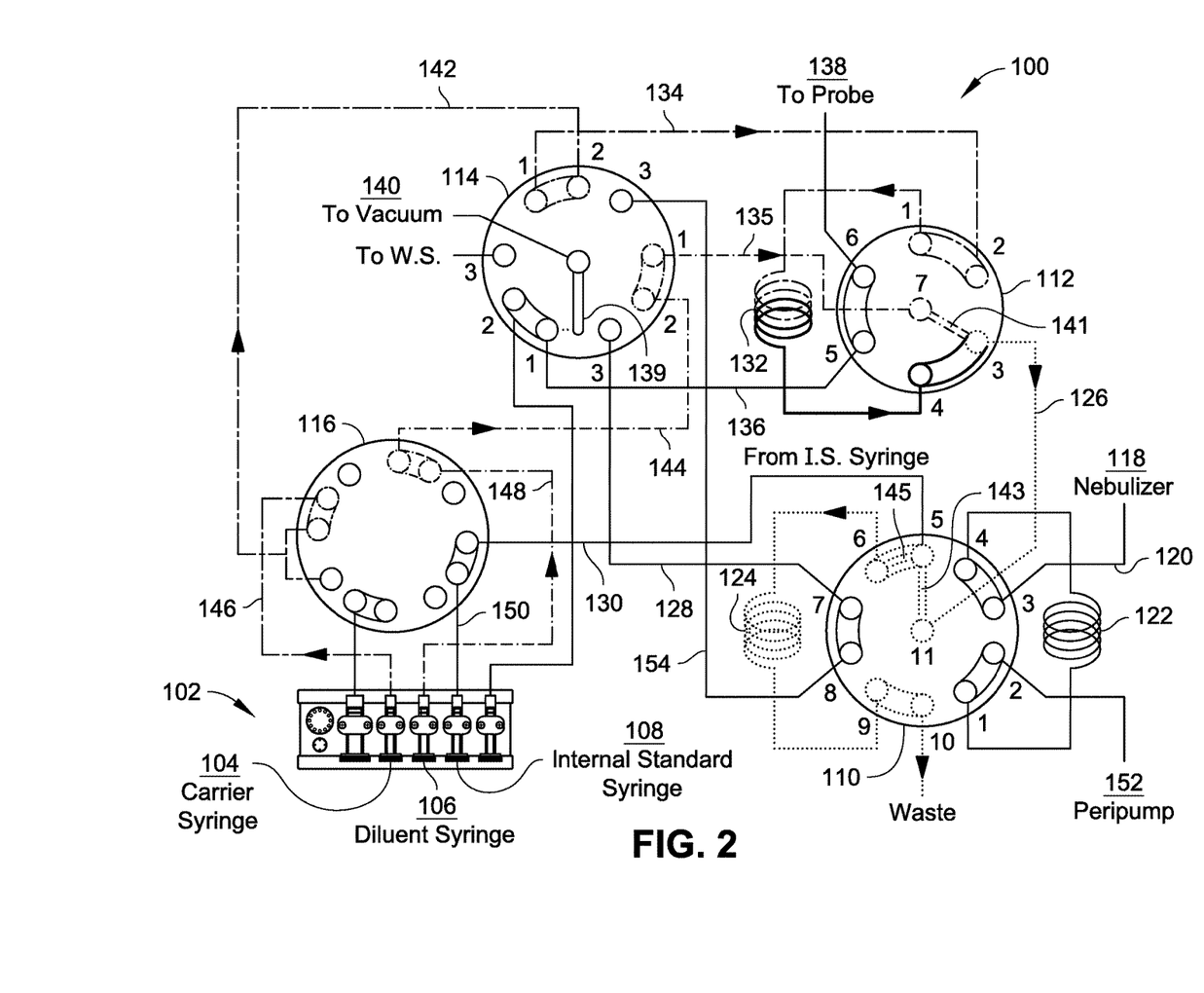
FIG. 2 is a schematic of a sample preparation system operating in a first stage of a second sample dilution mode, in accordance with an embodiment of this disclosure.
Figure 3:
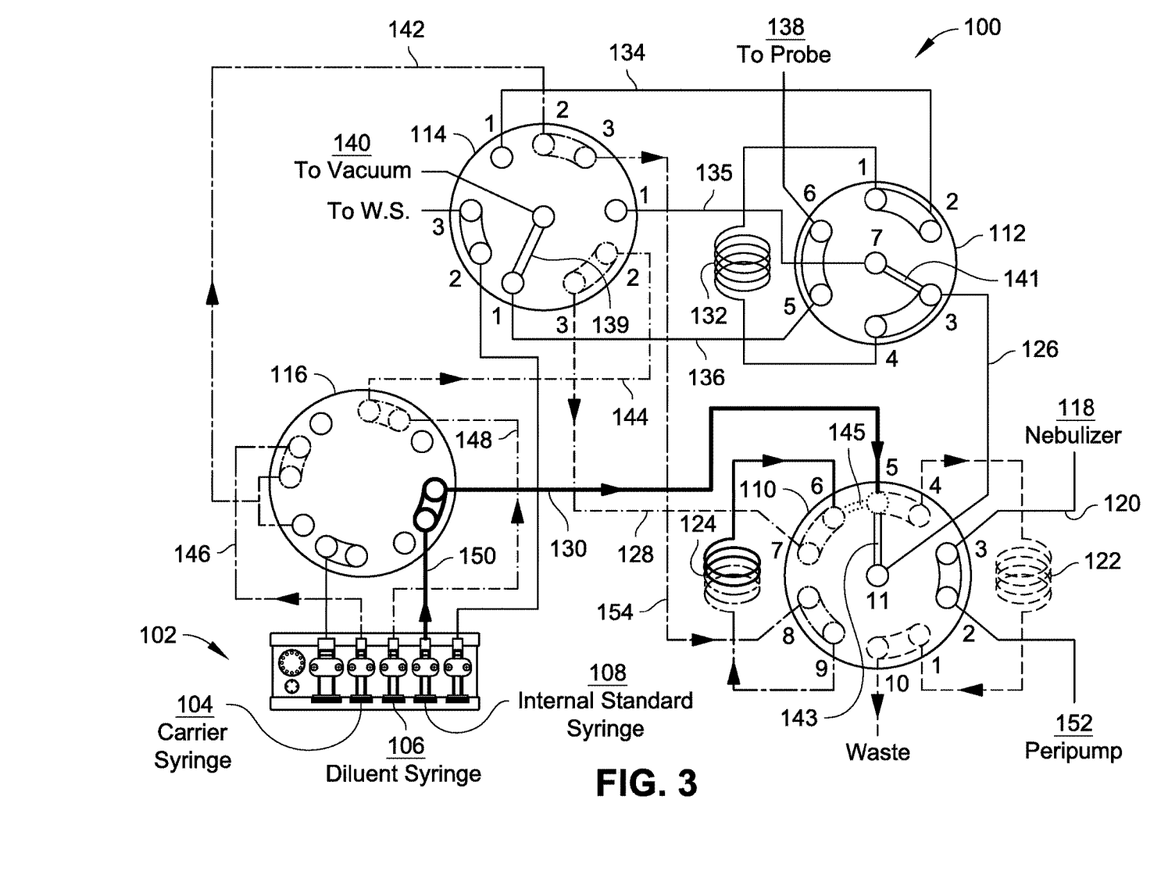
FIG. 3 is a schematic of a sample preparation system operating in a second stage of a second sample dilution mode, in accordance with an embodiment of this disclosure.

FIGS. 1 through 3 illustrate a sample preparation system ("system 100") in accordance with various embodiments of this disclosure, wherein the system 100 includes pump, valve, and control logic configurations that facilitate automatic, inline dilution of samples and standards for analytic analyses. Those skilled in the art will appreciate that the embodiments illustrated in the drawings and/or described herein may be modified or fully or partially combined to result in additional embodiments. Accordingly, the illustrated and described embodiments should be understood as explanatory and not as limitations of the present disclosure.

The system 100 provides structure and functionality for single stage and for dual stage dilution of fluids, where the system 100 can toggle between operating modes for various samples or standards during operation of the system 100. For instance, a controller of the system 100 can facilitate dilution of a first sample according to a first dilution factor through a single stage dilution operation, whereas the controller can facilitate dilution of a second sample according to a second dilution factor through a dual stage dilution operation. Example modes of operation are shown in FIGS. 1 through 3. For example, FIG. 1 illustrates the system 100 operating in a first sample dilution mode incorporating a single stage of dilution. FIGS. 2 and 3 illustrate the system 100 operating in a second sample dilution mode incorporating two stages of dilution. Additional modes of operation include, but are not limited to, sample loading mode to load a sample into the system 100, rinse mode to introduce a cleaning fluid into fluid lines of the system 100 (e.g., prior to dilution modes, subsequent to dilution modes, etc.), calibration mode to automatically build calibration curves, or the like.

In the embodiments illustrated in FIGS. 1 through 3, the system 100 is shown to include a plurality of syringe pumps 102 to drive fluids through fluid passageways of the system 100 (e.g., formed by fluid lines, fluid loops or coils, valve ports, valve channels, etc. in fluid communication with each other). While the system 100 is shown in the example embodiments having syringe pumps, the system 100 can incorporate any suitable type of pump for driving fluids through the system 100, including but not limited to, syringe pumps, peristaltic pumps, vacuum connections, or the like, or combinations thereof. For example, the plurality of syringe pumps 102 can include a first syringe pump 104 that controls a syringe to drive a carrier fluid through the system 100 (e.g., to push one or more samples or standards through the system 100), a second syringe pump 106 that controls a syringe to drive a diluent fluid (e.g., deionized water, ultra-pure water, etc.) through the system 100, and a third syringe pump 108 that controls a syringe to drive an internal standard through the system 100. The plurality of syringe pumps 102 can include additional syringe pumps to drive other fluids within the system 100, such as a syringe pump to drive a rinse or cleaning solution, calibration solutions, buffer solutions, eluent solutions, or the like. The size of the syringes utilized in the plurality of syringe pumps 102 can vary between each syringe pump or can be uniform in size. For example, the syringes can be between 0.5 mL and 20 mL in volume to drive relatively small volumes of fluids through the system to precisely control dilution factors, while avoiding requiring relatively large volumes of liquids (e.g., 50 mL or more) to provide the desired dilutions.

The plurality of syringe pumps 102 is fluidically coupled to multi-port valves (e.g., automated selection/selector valves) to direct the flow of fluids from the pumps within the system 100. For example, as shown in FIGS. 1 through 3, the system 100 includes a first selection valve 110, a second selection valve 112, a third selection valve 114, and a fourth selection valve 116, each of which is switchable between at least two flow configurations (e.g., via connection of flow channels between differing valve ports, where the positioning of the flow channels differs between differing flow configurations). Further, each of the first selection valve 110, the second selection valve 112, the third selection valve 114, and the fourth selection valve 116 is directly or indirectly in fluid communication with one or more pumps of the plurality of pumps 102.

The first selection valve 110 can provide an interface between the system 100 and ICP spectrometry instrumentation or other analytical instruments to provide a diluted sample to the ICP spectrometry instrumentation (e.g., via a nebulizer 118 in fluid communication with the first selection valve 110 via fluid line 120) or other analytical instruments. The first selection valve 110 is coupled to a first holding line 122 (e.g., forming a fluid holding loop or coil) via two ports of the first selection valve 110 (e.g., ports 1 and 4 in FIGS. 1-3). For instance, the system 100 can employ holding lines to hold a fluid at a valve while the valve switches flow configurations. The first selection valve 110 is also coupled to a second holding line 124 (e.g., forming a fluid holding loop or coil) via two ports of the first selection valve 110 (e.g., ports 6 and 9 in FIGS. 1-3). The first selection valve 110 is also in fluid communication with each of the second selection valve 112, the third selection valve 114, and the fourth selection valve 116. For example, the first selection valve 110 can be in fluid communication with the second selection valve 112 via fluid line 126, with the third selection valve 114 via fluid line 128, and with the fourth selection valve 116 via fluid line 130. The second selection valve 112 is coupled to a third holding line 132 (e.g., forming a fluid holding loop or coil) via two ports of the second selection valve 112 (e.g., ports 1 and 4 in FIGS. 1-3) and is in fluid communication with the third selection valve 114 and the fourth selection valve 116. For example, the second selection valve 112 can be in fluid communication with the third selection valve 114 via fluid lines 134, 135, and 136, and indirectly with the fourth selection valve 116 via fluid lines coupled with the third selection valve 114.

The second selection valve 112 can also be coupled with a sample source, such as a sample probe 138 of an autosampler configured for automatic selection of a particular sample, to draw a sample into the system 100 for sample preparation (e.g., dilution, standard addition, etc.) and analysis by the ICP spectrometry instrumentation. For example, the third selection valve 114 can be coupled with a vacuum source 140 to draw the sample from the sample probe 138 into the third holding line 132 (e.g., via fluid communication of fluid line 136 and a fluid channel 139 of the third selection valve 114 when coupled with port 1 of the third selection valve 114, and when the second selection valve 112 is in a load configuration (e.g., ports 1 and 6 in fluid communication, and ports 5 and 4 in fluid communication), shown in FIG. 3). Alternatively or additionally, a pump of the pump system 102 can be used to load a sample into the third holding line 132. The third selection valve 114 is in fluid communication with the fourth selection valve 116. For example, the third selection valve 114 can be in fluid communication with the fourth selection valve 116 via fluid lines 142 and 144. Alternatively or additionally, the system 100 can receive a sample or other fluid from another source, such as a fluid transfer line from another sample handling system, remote sampling system, or the like.

The fourth selection valve 116 is coupled with the plurality of syringe pumps 102 to receive the carrier, diluent, and internal standard fluids into the system 100. For example, the fourth selection valve 116 can be in fluid communication with the first syringe pump 104 to receive the carrier fluid via fluid line 146, with the second syringe pump 106 to receive the diluent fluid via fluid line 148, and with the third syringe pump 108 to receive the internal standard fluid via fluid line 150.

The system 100 includes at least two different operating modes to treat a sample once a sample is loaded into the third holding line 132 (an example of one possible loading procedure is provided above). A first operating mode is shown with reference to FIG. 1, where a single-stage inline dilution process occurs at the second selection valve 112. A second operating mode is shown with reference to FIGS. 2 and 3, where a dual-stage dilution process occurs (e.g., a first-stage dilution at the second selection valve 112 and a second-stage dilution at the first selection valve 110). Each operating mode will now be discussed.

Referring to FIG. 1, the system 100 is shown in an example sample dilution mode utilizing a single stage dilution. This sample dilution mode includes the fourth selection valve 116 in a dispense configuration to receive the carrier fluid from the first syringe pump 104 and transfer the carrier fluid to the third selection valve 114 (which is in a dispense configuration), where the third selection valve 114 permits flow of the carrier fluid to the second selection valve 112 to push the sample out of the third holding line 132 to be diluted (e.g., at port 3) by combining liquid flows with the diluent fluid received from the fourth selection valve 116 and transferred through the third selection valve 114. For instance, the diluent is received by the second valve 112 from the third selection valve 114 via fluid line 135 (e.g., coupled to port 7) through action of second syringe pump 106, wherein a channel 141 fluidically couples port 7 and port 3 to allow the diluent and the sample to mix at port 3 as the carrier fluid pushes the sample from the third holding line 132. The relative flow rates of the carrier fluid and the diluent fluid (facilitated by the first syringe pump 104 and the second syringe pump 106) can dictate the dilution factor of the sample. In an implementation, each pump of the plurality of syringe pumps 102 is computer controlled to precisely control the respective fluid flow rates to arrive at a desired dilution factor for a sample. The diluted sample is transferred from the second selection valve 112 to the first selection valve 102 where an optional internal standard can be added (e.g., at port 5) via reception of the internal standard by the fourth selection valve 116 and transfer to the first selection valve 110 (e.g., in a load configuration shown in FIG. 1). For instance, the diluted sample passes through fluid line 126 to port 11, wherein a channel 143 fluidically couples port 11 with port 5 to mix internal standard received via fluid line 130 from the fourth selection valve 116 with the diluted sample. The diluted sample is then introduced to the first holding line 122. The first selection valve 110 can then transition to an inject configuration whereby ports 3 and 4 are in fluid communication and ports 1 and 2 are in fluid communication (e.g., inject configuration of the first selection valve 110 shown in FIG. 2) to permit a pump 152 (e.g., a peristaltic pump) to push the diluted sample from the first holding line 122 to the nebulizer 118 for analysis by the ICP spectrometry instrumentation. In an implementation, the single-stage dilution operating mode provides dilution factors up to about one hundred times before the system 100 will operate under the dual-stage operating mode described below. However, this dilution factor is not limiting and other dilution factors can be utilized including, but not limited to, dilution factors exceeding one hundred times.

Referring to FIGS. 2 and 3, the system 100 is shown in an example sample dilution mode utilizing a dual-stage dilution (e.g., a first stage shown in FIG. 2 and a second stage shown in FIG. 3). The first stage sample dilution includes the fourth selection valve 116 in a dispense configuration to receive the carrier fluid from the first syringe pump 104 and transfer the carrier fluid to the third selection valve 114 (which is in a dispense configuration), where the third selection valve 114 permits flow of the carrier fluid to the second selection valve 112 (e.g., via fluid line 134) to push the sample out of the third holding line 132 to be diluted (e.g., at port 3) by combining liquid flows with the diluent fluid received from the fourth selection valve 116 and transferred through the third selection valve 114. For instance, the diluent is received by the second valve 112 from the third selection valve 114 via fluid line 135 (e.g., coupled to port 7) through action of the second syringe pump 106, wherein the channel 141 fluidically couples port 7 and port 3 to allow the diluent and the sample to mix at port 3 as the carrier fluid pushes the sample from the third holding line 132. The relative flow rates of the carrier fluid and the diluent fluid (facilitated by the first syringe pump 104 and the second syringe pump 106) can dictate the first dilution factor of the sample during the two-stage dilution. In an implementation, each pump of the plurality of syringe pumps 102 is computer controlled to precisely control the respective fluid flow rates to arrive at a desired dilution factor for a sample. The diluted sample is transferred from the second selection valve 112 to the first selection valve 110 (e.g., in an inject configuration) and loaded into the second holding line 124 for holding until the system 100 transitions to the second stage of the dual-stage dilution operating mode (shown in FIG. 3).

Referring to FIG. 3, the system 100 is shown providing flow path configurations to permit the second stage of dilution. For example, the fourth selection valve 116 is in the dispense configuration, the third selection valve 114 is in the load configuration, and the first selection valve 110 is in the load configuration. The second valve 112 can be bypassed to facilitate rinsing of one or more of the fluids lines associated therewith, loading of a new sample into the third holding line 132, or the like, or combinations thereof. As shown, the fourth selection valve 116 receives the carrier fluid from the first syringe pump 104 and transfers the carrier fluid to the third selection valve 114 (which is in the fill configuration), where the third selection valve 114 permits flow of the carrier fluid to the first selection valve 110 (e.g., via fluid line 154) to push the sample out of the second holding line 124 to be diluted (e.g., at port 6) by combining liquid flows with the diluent fluid received (e.g., via fluid line 128) from the third selection valve 114 via the fourth selection valve (e.g., via fluid line 144). The relative flow rates of the carrier fluid and the diluent fluid (facilitated by the first syringe pump 104 and the second syringe pump 106) can dictate the second dilution factor of the sample. In an implementation, each pump of the plurality of syringe pumps 102 is computer controlled to precisely control the respective fluid flow rates to arrive at a desired dilution factor for a sample. An optional internal standard can be added (e.g., at port 5) via reception of the internal standard by the fourth selection valve 116 and transfer to the first selection valve 110 (e.g., via fluid line 130), where the first selection valve 110 can include a channel 145 fluidically connecting ports 6 and 5. The diluted sample is then introduced to the first holding line 122. The first selection valve 110 can then transition to an inject configuration whereby ports 3 and 4 are in fluid communication and ports 1 and 2 are in fluid communication (e.g., as shown in FIG. 2) to permit a pump 152 (e.g., a peristaltic pump) to push the diluted sample from the first holding line 122 to the nebulizer 118 for analysis by the ICP spectrometry instrumentation. In an implementation, each dilution stage of the dual-stage dilution operating mode can have independent dilution factors, or can be the same dilution factor. For example, in an implementation each dilution stage can have a dilution factor up to about one hundred times dilution for a final dilution factor up to about ten thousand times. However, these dilution factors are not limiting and other dilution factors can be utilized including, but not limited to, dilution factors exceeding one hundred times for each dilution stage.

Figure 4:
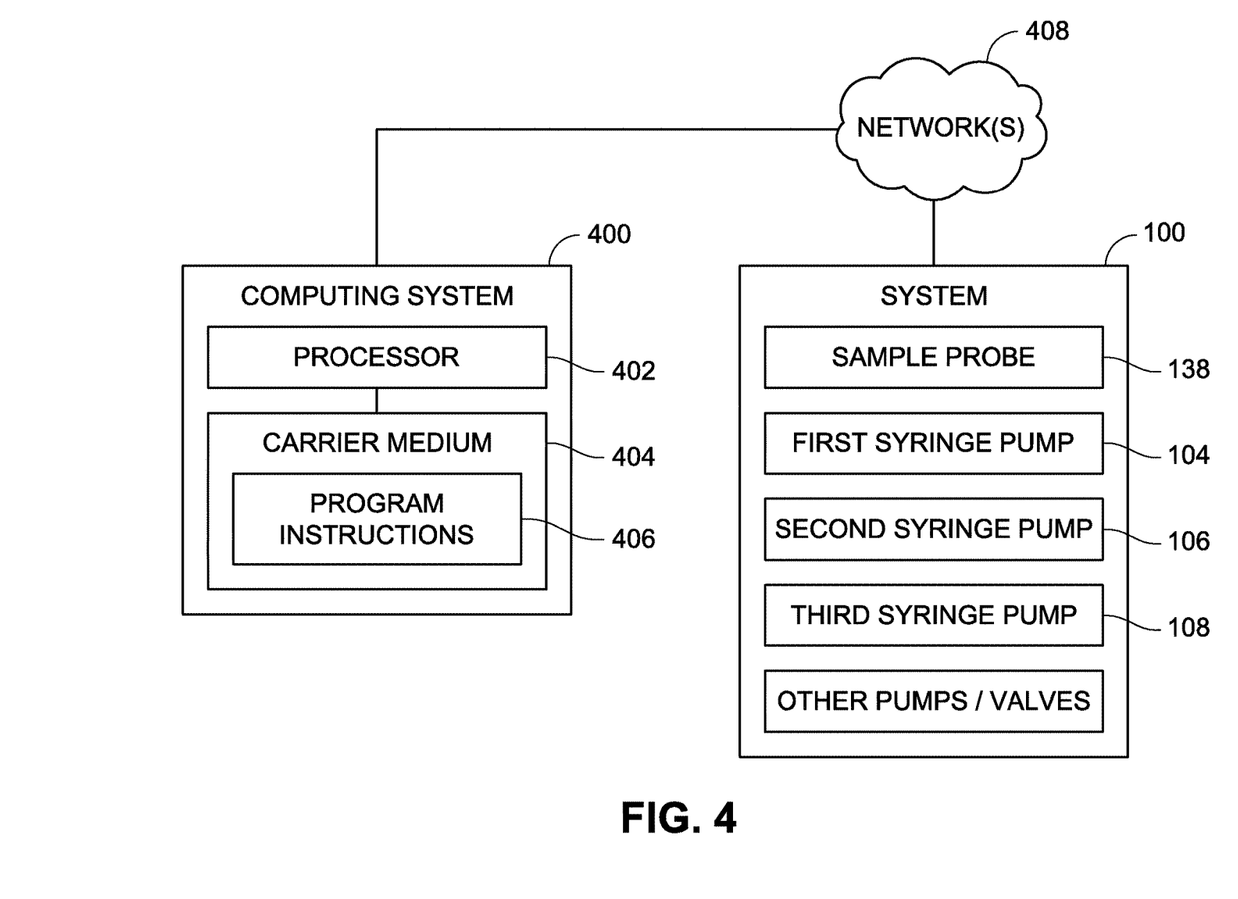
FIG. 4 is a schematic of a control protocol of a sample preparation system, such as the sample preparation system(s) described with reference to FIGS. 1-3.

Electromechanical devices (e.g., electrical motors, servos, actuators, or the like) may be coupled with or embedded within the selection valves, the syringe pumps, and combinations thereof to facilitate automated operation via control logic embedded within or externally driving the system 100. The electromechanical devices can be configured to cause the plurality of valves to direct fluid flows from syringes 104, 106, 108, and from other syringes, flow paths, etc., according to one or more modes of operation, such as those described herein. As shown in FIG. 4, the system 100 may include or be controlled by a computing system 400 having a processor 402 configured to execute computer readable program instructions 406 (i.e., the control logic) from a non-transitory carrier medium 404 (e.g., storage medium such as a flash drive, hard disk drive, solid-state disk drive, SD card, optical disk, or the like). The computing system 400 can be connected to various components of the system 100, either by direct connection, or through one or more network connections 408 (e.g., local area networking (LAN), wireless area networking (WAN or WLAN), one or more hub connections (e.g., USB hubs), and so forth). For example, the computing system 400 can be communicatively coupled to the sample probe 138 (or corresponding autosampler), syringe pump 104, syringe pump 106, syringe pump 108, and any of the various pumps or selection valves described herein. The program instructions 406, when executing by processor 402, can cause the computing system 400 to control the system 100 (e.g., control the pumps and selection valves) according to one or more modes of operation, as described herein. In an implementation, the computing system 400 implements a sample scheduler to permit a user to enter a desired dilution factor independently for a plurality of samples to be analyzed in series. For example, a user can input a desired final dilution factor for a sample and the processor 402 can determine whether a single-stage or dual-stage dilution operating mode is preferred for the desired final dilution factor. If a single-stage dilution operating mode is sufficient (e.g., the dilution factor does not exceed a threshold dilution factor (e.g., a dilution factor where the resolution of the syringe pumps is not sufficient for a single-stage dilution), such as 100 times dilution), then the computing system 400 will automatically control the system to provide the sample dilution according to the single-stage dilution operating mode (e.g., as shown in FIG. 1). If a single-stage dilution operating mode is not sufficient (e.g., the dilution factor exceeds the threshold dilution factor), then the computing system 400 will automatically control the system 100 to provide the sample dilution according to the dual-stage dilution operating mode (e.g., as shown in FIGS. 2 and 3).

It should be recognized that the various functions, control operations, processing blocks, or steps described throughout the present disclosure may be carried out by any combination of hardware, software, or firmware. In some embodiments, various steps or functions are carried out by one or more of the following: electronic circuitry, logic gates, multiplexers, a programmable logic device, an application-specific integrated circuit (ASIC), a controller/microcontroller, or a computing system. A computing system may include, but is not limited to, a personal computing system, a mobile computing device, mainframe computing system, workstation, image computer, parallel processor, or any other device known in the art. In general, the term "computing system" is broadly defined to encompass any device having one or more processors, which execute instructions from a carrier medium.

Program instructions implementing functions, control operations, processing blocks, or steps, such as those manifested by embodiments described herein, may be transmitted over or stored on carrier medium. The carrier medium may be a transmission medium, such as, but not limited to, a wire, cable, or wireless transmission link. The carrier medium may also include a non-transitory signal bearing medium or storage medium such as, but not limited to, a read-only memory, a random access memory, a magnetic or optical disk, a solid-state or flash memory device, or a magnetic tape.

Furthermore, it is to be understood that the invention is defined by the appended claims. Although embodiments of this invention have been illustrated, it is apparent that various modifications may be made by those skilled in the art without departing from the scope and spirit of the disclosure.

What is claimed is:

1. A system for single-stage and dual-stage dilution of a sample, comprising:
   a first pump configured to drive a carrier fluid;
   a second pump configured to drive a diluent; and
   a plurality of selection valves fluidically coupled with the first pump and the second pump, the plurality of selection valves configured to provide a single-stage sample dilution of a sample according to a first operating mode and to provide a dual-stage sample dilution of the sample according to a second operating mode, the plurality of selection valves including at least a first valve, a second valve, and a third valve, wherein the first valve is fluidically coupled with the second valve and the third valve, wherein the second valve is fluidically coupled with the first valve and the third valve, wherein the second valve includes a mixing port coupled to two fluid flow pathways to mix the sample and the diluent in the first operating mode and the second operating mode to provide a diluted sample, and wherein the first valve includes a mixing port coupled to two fluid flow pathways to mix the diluted sample and the diluent in the second operating mode.

2. The system of claim 1, wherein the second valve is coupled to a first fluid holding line, the second valve having a first fluid flow configuration that fluidically couples the first fluid holding line with a sample source to load the sample into the first fluid holding line, the second valve having a second fluid flow configuration that fluidically couples the first pump with the first fluid holding line to drive carrier fluid through the first fluid holding line.

3. The system of claim 2, wherein the second valve is in the second fluid flow configuration during each of the first operating mode and the second operating mode.

4. The system of claim 2, wherein the first valve is coupled to a second fluid holding line, the first valve having a first fluid flow configuration that fluidically couples the second fluid holding line with the second valve to direct the diluted sample into the second fluid holding line, the first valve having a second fluid flow configuration that fluidically couples the first pump with the second fluid holding line to drive carrier fluid through the second fluid holding line.

5. The system of claim 4, wherein the first valve is coupled to a third fluid holding line, wherein the third fluid holding line is fluidically coupled to the second holding line when the first valve is in the second fluid flow configuration.

6. The system of claim 5, wherein the third fluid holding line is fluidically coupled with an analysis instrument when the first valve is in the first fluid flow configuration.

7. The system of claim 6, wherein the analysis instrument includes an inductively coupled plasma analysis instrument.

8. The system of claim 1, further comprising:
a third pump configured to drive an internal standard, the third pump in fluid communication with the first valve during each of the first operating mode and the second operating mode.

9. The system of claim 8, wherein the first valve includes a second mixing port coupled to two fluid flow pathways to mix the internal standard and the diluted sample following introduction of the diluted sample and the diluent in the second operating mode.

10. The system of claim 1, wherein the third valve includes a first fluid flow configuration that fluidically couples the first pump with the second valve, and wherein the third valve includes a second fluid flow configuration that fluidically couples the first pump with the first valve.

11. The system of claim 10, wherein the first fluid flow configuration of the third valve further fluidically couples the second pump with the second valve, and wherein the second fluid flow configuration of the third valve fluidically couples the second pump with the first valve.

12. The system of claim 11, wherein the third valve is in the first fluid flow configuration during the first operating mode and during a first portion of the second operating mode, and wherein the third valve is in the second fluid flow configuration during a second portion of the second operating mode.

13. A system for single-stage and dual-stage dilution of a sample, comprising:
a first pump configured to drive a carrier fluid;
a second pump configured to drive a diluent; and
a plurality of selection valves fluidically coupled with the first pump and the second pump, the plurality of selection valves configured to provide a single-stage sample dilution of a sample according to a first operating mode and to provide a dual-stage sample dilution of the sample according to a second operating mode, the plurality of selection valves including at least a first valve and a second valve, wherein the first valve is fluidically coupled with the second valve, wherein the second valve includes a mixing port coupled to two fluid flow pathways to mix the sample and the diluent in the first operating mode and the second operating mode to provide a diluted sample, and wherein the first valve includes a mixing port coupled to two fluid flow pathways to mix the diluted sample and the diluent in the second operating mode.

14. The system of claim 13, wherein the second valve is coupled to a first fluid holding line, the second valve having a first fluid flow configuration that fluidically couples the first fluid holding line with a sample source to load the sample into the first fluid holding line, the second valve having a second fluid flow configuration that fluidically couples the first pump with the first fluid holding line to drive carrier fluid through the first fluid holding line.

15. The system of claim 14, wherein the second valve is in the second fluid flow configuration during each of the first operating mode and the second operating mode.

16. The system of claim 14, wherein the first valve is coupled to a second fluid holding line, the first valve having a first fluid flow configuration that fluidically couples the second fluid holding line with the second valve to direct the diluted sample into the second fluid holding line, the first valve having a second fluid flow configuration that fluidically couples the first pump with the second fluid holding line to drive carrier fluid through the second fluid holding line.

17. The system of claim 16, wherein the first valve is coupled to a third fluid holding line, wherein the third fluid holding line is fluidically coupled to the second holding line when the first valve is in the second fluid flow configuration.

18. The system of claim 17, wherein the third fluid holding line is fluidically coupled with an analysis instrument when the first valve is in the first fluid flow configuration.

19. The system of claim 18, wherein the analysis instrument includes an inductively coupled plasma analysis instrument.

20. The system of claim 13, further comprising:
a third pump configured to drive an internal standard, the third pump in fluid communication with the first valve during each of the first operating mode and the second operating mode.

* * * * *